(12) United States Patent
Giuseppin et al.

(10) Patent No.: US 9,102,749 B2
(45) Date of Patent: Aug. 11, 2015

(54) PROTEIN GEL FORMATION

(75) Inventors: Marco Luigi Federico Giuseppin, Gieten (NL); Wybren Bakker, Groningen (NL)

(73) Assignee: COOPERATIE AVEBE U.A., Veendam (NL)

( * ) Notice: Subject to any disclaimer, the term of this patent is extended or adjusted under 35 U.S.C. 154(b) by 1203 days.

(21) Appl. No.: 12/514,210

(22) PCT Filed: Oct. 25, 2007

(86) PCT No.: PCT/NL2007/050512
§ 371 (c)(1),
(2), (4) Date: Aug. 13, 2009

(87) PCT Pub. No.: WO2008/069649
PCT Pub. Date: Jun. 12, 2008

(65) Prior Publication Data
US 2010/0003394 A1    Jan. 7, 2010

(30) Foreign Application Priority Data

Nov. 10, 2006  (EP) .................................... 06077000
Mar. 12, 2007  (EP) .................................... 07103954

(51) Int. Cl.
*A23L 1/305*     (2006.01)
*C07K 14/415*    (2006.01)
(Continued)

(52) U.S. Cl.
CPC ............... *C07K 14/415* (2013.01); *A23J 1/006* (2013.01); *A23J 1/16* (2013.01); *A23J 3/14* (2013.01); *A23L 1/3055* (2013.01); *A23L 2/52* (2013.01); *A23L 2/66* (2013.01)

(58) Field of Classification Search
CPC ............................ C07K 14/415; A23L 1/3055
USPC ......................................................... 426/578
See application file for complete search history.

(56) References Cited

U.S. PATENT DOCUMENTS

| 4,424,151 A | 1/1984 | Grealy et al. | |
|---|---|---|---|
| 2004/0175481 A1* | 9/2004 | Marchal et al. | 426/615 |
| 2006/0204454 A1* | 9/2006 | Veerman | 424/50 |

FOREIGN PATENT DOCUMENTS

| EP | 1264545 A1 | 12/2002 |
|---|---|---|
| EP | 1920662 A1 | 5/2008 |

(Continued)

OTHER PUBLICATIONS

Friedli, Georges-Louis. "Proteins" retrieved from Web Archive www.friedli.com and available on Aug. 21, 2006. pp. 1-28.*

(Continued)

*Primary Examiner* — Jenna A Watts
(74) *Attorney, Agent, or Firm* — Hoffmann & Baron, LLP

(57) ABSTRACT

The invention is directed to a method of forming a gel, a gel obtainable by said method, a heat treated native potato protease inhibitor, the use of said protease inhibitor, and a foodstuff comprising said gel or said protease inhibitor. The method comprises the subsequent steps of: providing a solution of native potato protease inhibitor isolate having an isoelectric point of more than 6.0 and a molecular weight of less than 35 kDa; subjecting the native potato protease inhibitor solution to a heat treatment to a temperature of 65-121° C. for at least 10 minutes, or an UHT treatment at temperatures above 121° C., at an ionic strength of less than 60 mM and a pH of less than 4.5 yielding a heat treated native potato protease inhibitor solution; and setting the ionic strength of the native potato protease inhibitor solution to more than 60 mM.

17 Claims, 1 Drawing Sheet

(51) Int. Cl.
*A23J 1/00* (2006.01)
*A23J 1/16* (2006.01)
*A23J 3/14* (2006.01)
*A23L 2/52* (2006.01)
*A23L 2/66* (2006.01)

(56) References Cited

FOREIGN PATENT DOCUMENTS

| | | |
|---|---|---|
| WO | 9742834 A1 | 11/1997 |
| WO | 9959623 A1 | 11/1999 |
| WO | 2004049819 A2 | 6/2004 |

OTHER PUBLICATIONS van Den Broek, Lambertus A.M., et al. "Structural Characterization of Potato Protease Inhibitor 1 after Expression in *Pichia pastoris*". J. Agric. Food Chem 2004, 52, 4928-4934.*

Ralet, Marie-Christine, et al., "Fractionation of Potato Proteins: Solubility, Thermal Coagulation and Emulsifying Properties", Lebensmittel Wissenschaft Und Technologie, vol. 33, No. 5, pp. 380-387; 2000.

Knorr, D., "Functional Properties of Potato Protein Concentrates", Lebensmittel Wissenschaft Und Technologie, vol. 13, No. 6, pp. 297-301; 1980.

Van Koningsveld, Gerrit A., et al., "Effects of pH and Heat Treatments on the Structure and Solubility of Potato Proteins in Different Preparations", Journal of Agriculture Food Chemistry, vol. 49, pp. 4889-4897; 2001.

Pouvreau, L., et al., "Relative Abundance and Inhibitory Distribution of Protease Inhibitors in Potato Juice from cv. Elkana", Journal of Agriculture Food Chemistry, vol. 49, pp. 2864-2874; 2001.

Pots, Andre M., et al., "The Effect of Storage of Whole Potatoes of Three Cultivars on the Patatin and Protease Inhibitor Content; a Study Using Capillary Electrophoresis and MALDI-TOF Mass Spectrometry", Journal of the Science of Food and Agriculture, vol. 79, pp. 1557-1564, 1999.

Creusot, Nathalie, "Enzyme-induced Aggregation of Whey Proteins with *Bacillus licheniformis* Protease", PhD thesis, Wageningen University, The Netherlands, 2006.

Weinbreck, Fanny, "Whey Protein / Polysaccharide Coacervatives: Structure and Dynmics", PhD thesis, Utrecht University, 2004.

* cited by examiner

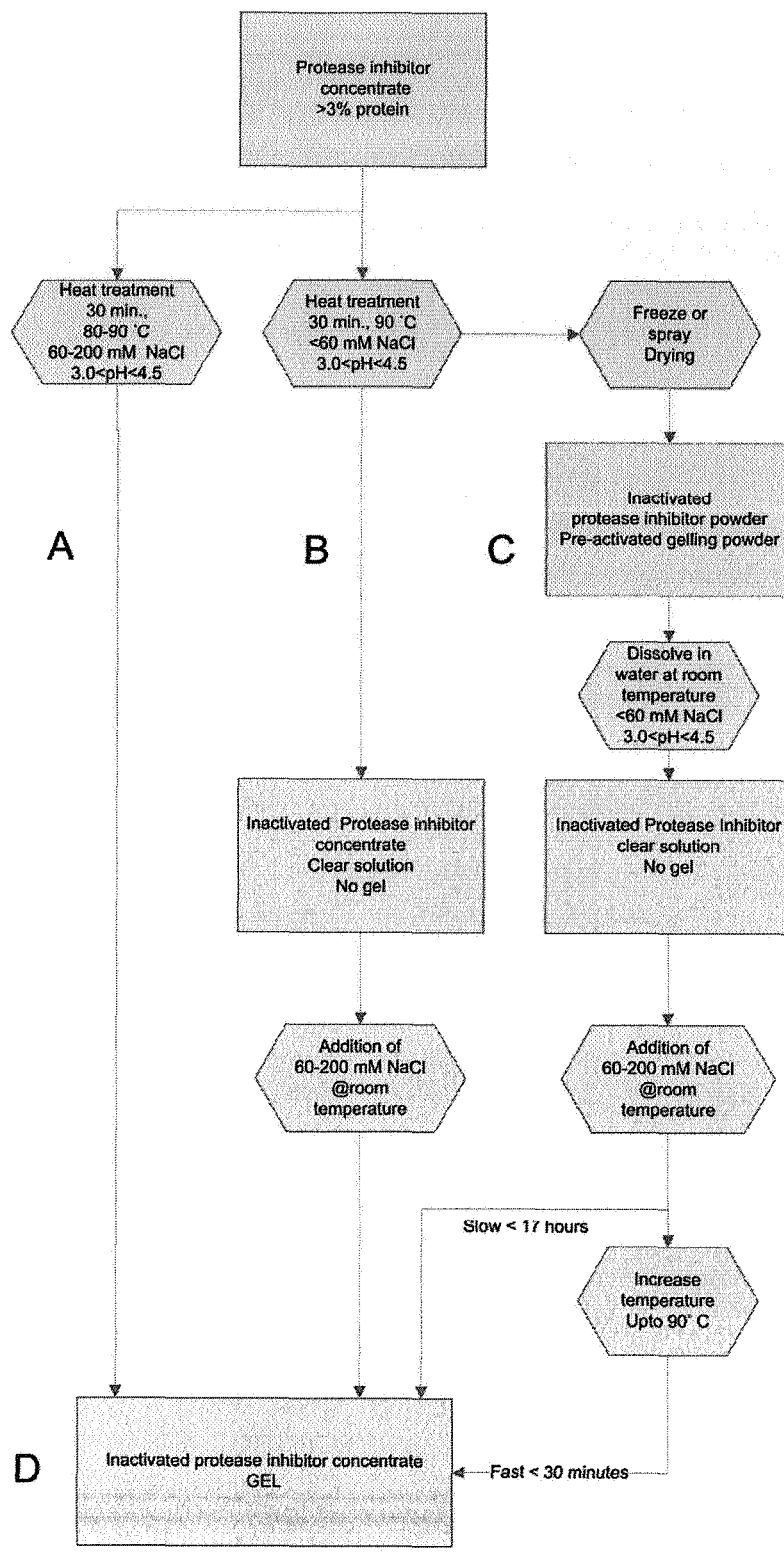

PROTEIN GEL FORMATION

This application is the U.S. National Phase of, and Applicants claim priority from, International Application Number PCT/NL2007/050512 filed 25 Oct. 2007, European Patent Application No. 06077000.5 filed 10 Nov. 2006 and European Patent Application No. 07103954.9 filed 12 Mar. 2007, all of which are incorporated herein by reference.

BACKGROUND OF THE INVENTION

The invention is directed to a method of forming a gel, to heat treated native potato protease inhibitor isolate, to the use of said protease inhibitor isolate, and to a foodstuff comprising said gel or protease inhibitor isolate.

The undiluted juice from potato tuber is called potato fruit juice, whereas the diluted juice is referred to as potato fruit water. Potato fruit juice may be produced by washing and rasping potatoes and separating the starch and fibres by various techniques, such as centrisieves, hydrocyclones and decanters. Fresh potato fruit juice is a complex mixture of soluble and insoluble material comprising proteins, starch, minerals, toxic glycoalkaloids and monomeric and polymeric reactive phenols.

Fresh potato fruit juice is however not very stable. Oxidation leads to conversion of phenolic compounds into quinones which rapidly combine into a dark polymer residue. During the oxidation process the potato proteins can partially crosslink, which dramatically reduces the solubility of the proteins. The complexity and instability of the potato fruit juice makes the separation and isolation of minimally denatured or modified proteins a complicated and economically demanding process.

Native potato proteins can tentatively be divided into the following three classes: (i) the patatin family, highly homologous acidic 43 kDa glycoproteins (40-50 wt. % of the potato proteins), (ii) basic 5-25 kDa protease inhibitors (30-40 wt. % of the potato proteins) and (iii) other proteins mostly high molecular weight proteins (10-20 wt. % of the potato proteins) (Pots et al., *J. Sci. Food. Agric.* 1999, 79, 1557-1564).

Protease inhibitors can be divided into different groups based on their molecular weight. The different groups of protease inhibitors are identified as protease inhibitor I (molecular weight of about 39 kDa), carboxypeptidase inhibitor (molecular weight of about 4100 Da), protease inhibitors IIa and IIb (molecular weight of about 20.7 kDa), and protease inhibitor A5 (molecular weight of about 26 kDa). The ratio of these different groups of protease inhibitors in the total potato protein depends on the potato variety. Protease inhibitors from potato have a broad range of potentially important applications. Protease inhibitors have for instance shown to be useful in the treatment of diabetes, for eliciting satiety in mammals, for reducing the risk of skin cancer, for inhibiting the growth of bacteria, and for preventing or treating inflammation on pruritis of skin and intestine, see for instance WO-A-99/059623.

One of the major drawbacks of the potato protein as presently used is that the recovery of potato protein in pure form has shown to be very difficult. Most methods of the prior art yield potato proteins in low purity, are not selective and/or are unable to separate the different functionalities.

The non pre-published European patent application 06077000.5 describes a selective and efficient process for the isolation of native potato protein and the different native potato protein fractions with a high degree of purity. This patent application also mentions that native potato protein patatin isolate and native potato protease inhibitor isolate can be used as a gelling agent in a food product.

For gel formation, various types of protein gelling mechanisms and compounds are known and applied in the prior art. Typical examples include thermogelling (for instance gelatine can form a gel after cooling a solution), acid induced gelling by denaturation and flocculation, and gel formation by partial degradation of proteins using enzymes. Conversion processes have also been described for instance by Creusot (PhD thesis, "Enzyme-induced aggregation of whey proteins with *Bacillus licheniformis* protease", Wageningen University, The Netherlands, 2006), wherein a gel is formed via one step (native gel→gel) or two step (native protein→pre-aggregate→gel) gel formation processes.

Particularly in sterilised foods, a control of the gel formation is important. The currently available proteins show a wide variety of gelling behaviour, but do not show a heat independent gel formation. This would be desirable for applications in high protein foods and acid foods.

In addition, it is desirable to replace animal proteins and/or allergenic proteins such as gelatine, egg and whey/milk proteins, in consumer products.

Furthermore, it is desirable to have an easy gel formation process with mild processing.

SUMMARY OF THE INVENTION

Accordingly, it is an object of the invention to provide a method of forming a gel which allows a control of the gel properties, such as the transparency and/or viscosity.

Another object of the invention is to provide a method of forming a gel using a protein that shows heat independent gel formation.

One or more of these objects are met by the method of the present invention in which a specific native potato protein isolate is applied.

Accordingly, in a first aspect the present invention is directed to a method of forming a gel, comprising the steps of:
  providing an aqueous solution of native potato protease inhibitor isolate having an isoelectric point of more than 6.0, preferably more than 7.0, and a molecular weight of less than 35 kDa, preferably less than 23 kDa;
  subjecting the native potato protease inhibitor solution to a heat treatment at a temperature of 65-121° C. for at least 10 minutes at an ionic strength of less than 60 mM and a pH of less than 4.5 yielding a heat treated native potato protease inhibitor solution; and
  setting the ionic strength of the native potato protease inhibitor solution to more than 60 mM.

The steps of the method according to the invention may be carried out in any order, but are preferably carried out subsequently.

The inventors found that this gel formation method is heat independent. Furthermore, they surprisingly found that the gel properties can be controlled by the ionic strength set.

DETAILED DESCRIPTION OF THE INVENTION

The term "protease inhibitor isolate" as used in this application is meant to refer to a purified native potato protein protease inhibitor isolate which can be obtained according to process described in the non prepublished European patent application 06077000.5. The protease inhibitor isolate comprises a majority of protease inhibitors (preferably more than 85% of all proteins, as measured by gel electrophoresis analysis) and a minority of other proteins. The native potato protease inhibitor isolate has an isoelectric point of above 6.0 and a molecular weight of less than 35 kDa.

The term "protease inhibitor" as used in this application is meant to include different types of protease inhibitors and other proteins that are present in the native potato protease inhibitor isolate.

The native potato protease inhibitor isolate to be used in the method of the present invention can be obtained by the process described in the non pre-published European patent application 06077000.5. The contents of this patent application are hereby incorporated by reference.

According to the process of the non pre-published European patent application 06077000.5 potato fruit juice is preferably first pre-treated by a divalent metal cation at a pH of 7-9 to flocculate undesired material. Then, the flocks are separated from the potato fruit juice by centrifugation. The supernatant is subjected to expanded bed chromatography operated at a pH of less than 11 and a temperature of 5-35° C. using an adsorbent which binds native potato protein. Finally, the native potato protein is eluted from the adsorbent with a suitable eluent. This process yields highly pure native potato protein isolate with a minimum of denatured protein and stable solubility.

If mixed-mode adsorbentia are used, the native potato proteins can be fractionated to both isoelectric point and molecular weight. This allows to separate the patatin and protease inhibitor fractions. The mixed mode adsorbentia can be used in two modes. The first mode is selective elution, which comes down to binding of essentially all of the potato protein and subsequently eluting a first desired potato protein fraction with an appropriate buffer and eluting a second desired potato protein fraction with another appropriate buffer. The second mode is selective adsorption, which comes down to binding of a first desired potato protein fraction on one column at an elevated pH, and adjusting the effluent to a lower pH so that a second desired potato protein fraction can bind on a second column. The protease inhibitors are eluted at a pH of 5.8-12.0, preferably at a pH of 6.0-9.5.

After elution, the native potato proteins may be concentrated by ultrafiltration. This may further reduce the amount of undesired compounds, such as glycoalkaloids. For protease inhibitors the ultrafiltration is typically carried out at a pH of 3-7, preferably 3.2-4.5. Apart from ultrafiltration other concentration methods can be applied such as evaporation, freeze concentration, or isoelectric precipitation using carbon dioxide.

It is preferred that the native potato protease inhibitor isolate to be used in the present invention has a glycoalkaloid concentration of less than 150 ppm. The native potato protease inhibitors may be isolated from any potato type. Typically, the protease inhibitors are isolated from *Solanum tuberosum*.

According to the present invention, the native potato protease inhibitor isolate has an isoelectric point of above 6.0, preferably above 7.0. This provides enough charges to have the desired gel formation properties. For practical reasons, it is not preferred that the isoelectric point is higher than 9.0.

Small protein molecules are usually more stable than proteins with a high molecular weight. Therefore, it is desirable that the protease inhibitor molecules are relatively small. The native potato protease inhibitor isolate to be used in the method of the present invention has a molecular weight of less than 35 kDa, preferably less than 23 kDa.

In addition, it is preferred that the proteins are compact. This also is advantageous for the stability of the proteins. Accordingly, the protease inhibitors may have one or more intramolecular disulphide bridges. The disulphide bridges aid in providing a strong protein configuration after heating. In order not to rupture the disulphide bridges in the native potato protease inhibitors, it is not recommended to use reducing conditions when purifying the isolate.

Further, it is advantageous that the pH dependence of the protein charge is limited in order to avoid unfolding of the protein at low pH. A relatively low protein charge at low pH is desired. The charge can be estimated using the amino acid sequence of the protein and protein modelling tools such as Protein Calculator (Scripps research institute).

According to the method of the invention a solution is prepared from the native potato protease inhibitor isolate. Preferably the concentration of native potato protease inhibitors is at least 3 wt. %, based on the total weight of the solution, preferably at least 4 wt %. Preferably an aqueous solution is used for food applications. Organic solvents may be considered for non-food applications.

The native potato protease inhibitor solution is subjected to a heat treatment. During the heat treatment a small configuration change is induced in the protease inhibitor molecules. The protease inhibitor activity of e.g. trypsin inhibitor is thereby strongly reduced. The heat treatment typically involves heating to a temperature of 65-121° C., preferably to a temperature of 85-100° C., or an UHT (Ultra High Temperature) treatment at temperatures above 121° C. During an UHT treatment the temperature typically is not above 175° C., preferably not above 160° C., for a short time period of typically 0.5-10 seconds, preferably 1-5 seconds, most preferably 1-2 seconds. A typical UHT treatment is known by the person skilled in the art. If the temperature is lower than 65° C., then the configuration change is insufficient. If the temperature is higher than 121° C., the protein molecules degrade, unless an UHT treatment is used. It is preferred that the native protease inhibitor solution is heated for at least 10 minutes. Preferably, the native protease inhibitor solution is heated for 15-60 minutes, more preferably 20-45 minutes.

The heat treatment is carried out at an ionic strength of less than 60 mM and a pH of less than 4.5. Preferably the pH is 3.0-4.5. During this treatment no gel is formed.

The heat treated native potato protease inhibitor thus obtained is an intermediate product of the final gel. Accordingly, in one aspect the invention is directed to heat treated native potato protease inhibitor obtainable by the method of the invention. This protease inhibitor comprises native potato protease inhibitor isolate having an isoelectric point of more than 6.0, preferably above 7.0 and a molecular weight of less than 35 kDa, preferably less than 23 kDa. The heat treatment comprises heating to a temperature of 65-121° C. for at least 10 minutes at an ionic strength of less than 60 mM and a pH of less than 4.5. Alternatively, the solution can be treated in an UHT treatment at temperatures above 121° C. at a pH of less than 4.5, preferably 3.0-4.5. This heat treated native potato inhibitor can advantageously be used as a gelling agent.

Therefore, in one aspect the invention is directed to the use of the heat treated native potato protease inhibitor as a gelling agent, for example in foods and industrial pharmaceutical products. The heat treated native potato protease inhibitor solution can be used as such, concentrated further, or as a freeze dried, flash dried or spray dried powder.

In order to form a gel the ionic strength of the heat treated native potato protease inhibitor solution is set at a value of more than 60 mM. In one embodiment the ionic strength is set by the addition of at least one salt to the heat treated native potato protease inhibitor solution. In another embodiment the ionic strength is set to more than 60 mM by adding the heat treated native potato protease inhibitor solution to a composition (such as a food composition) comprising at least one salt. In another embodiment the ionic strength is set to more than 60 mM by first adding an amount of salt to the heat treated native potato protease inhibitor solution and subsequently adding this protease inhibitor solution to a composition comprising an amount of salt.

Preferably the ionic strength is set to 60-400 mM. Nevertheless, for technical applications and soy sauce-like applications an ionic strength of up to 3000 mM, or even up to 4000 mM may be used. Setting the ionic strength to more than 60 mM results in the formation of a gel. Such a gel is commonly referred to as an ionogenic gel, in contrast to a thermally induced gel or acid induced gel. The ionic strength can be set to more than 60 mM at room temperature, but it can also be set at elevated temperatures such as 65-121° C., or an UHT treatment at temperatures above 121° C.

The advantageous characteristics of native potato protease inhibitor combined with the application of a food compatible salt enables an alternative way to instantaneously form gels in foods. This avoids the use of heating or cooling of the products to form gels or higher protein based viscosity. The rate of gel formation depends strongly on the salt concentration, pH and protein concentration used.

In principle any type of salt, comprising mono or divalent cations, can be used for setting the ionic strength to more than 60 mM, either by addition to the heat treated native potato protease inhibitor solution or in a composition to which the heat treated native potato protease inhibitor solution is added. Examples include for instance salts comprising sodium, potassium, and calcium cations. Also combinations of different salts are possible. The effect appears to be most pronounced for the calcium cation. However, the sodium cation is advantageous in combination with milk and soy proteins, which tend to precipitate in the presence of calcium.

An important advantage of the present invention is that the gel properties such as transparency and/or viscosity can be controlled by the ionic strength set. Accordingly, by changing the ionic strength, for instance by changing the amount of salt added, one can prepare a clear, an opaque, or a milky gel, and at the same time influence the viscosity of the gel.

The positive charge at a wide pH range is important for the effective formation of coacervates. Coacervates are complexes formed between positively charged proteins and a negatively charged polysaccharide (e.g. F. Weinbreck "Whey protein/polysaccharide coacervates: structure and dynamics", PhD thesis, Utrecht University 2004). Whey proteins, with an isoelectric point of 5.2, have a limited pH range up to pH 5.2 for which a positive charge allows the formation of complexes with negatively charged polyharides. By the higher isoelectric point of the protease inhibitor proteins isolate the effective pH of coacervation formation can be extended to higher pH values of 6.0 up to 7.0. The heat pre-treated protease inhibitors can be used to coacervate heat labile compounds such as flavours, fatty acids, lipids and enzymes.

In a special embodiment, the heat treated native potato protease inhibitor solution is freeze dried, flash dried or spray dried to yield an inactivated native potato protease inhibitor powder. This dry powder is stable and can be stored over long periods.

At the time when the powder is to be processed, the inactivated native potato protease inhibitor powder can be dissolved to form a solution with an ionic strength of less than 60 mM and a pH of less than 4.5. Dissolving the powder may be done at room temperature. A gel is formed after setting the ionic strength of the solution to more than 60 mM.

In an optional step the gel formation time can be reduced by heating to a temperature of 65-121° C., preferably 85-100° C., or an UHT treatment at temperatures above 121° C., after setting the ionic strength to more than 60 mM.

The gel formation according to the method of the present invention is reversible. When the gel is diluted until the ionic strength is less than 60 mM the gel slowly dissolves again.

In a further aspect, the invention is directed to a gel obtainable by the method of the invention. It has been found that such a gel has a short and smooth structure. Its clarity can be controlled by the salt and concentration of the protease inhibitor isolate.

The invention is also directed to a food product comprising the gel or the heat treated native potato protease inhibitor obtainable by the method of the invention. In particular, this involves food products with ionic strengths of more than 60 mM. The food product can be in the form of a drink, preferably a high protein drink or a sports drink. The soft gels can be employed both as viscosifier and protein fortifier.

BRIEF DESCRIPTION OF DRAWINGS

FIG. 1 is a graphical representation of the examples that follow, and they are not intended to limit the invention.

EXAMPLES

Example 1

Salt Induced Gel Formation in a Heat Treated Protease Inhibitor Solution

Gels were formed using three routes. As a starting material a protease inhibitor isolate concentrate with a concentration corresponding with 20° Brix and pH 3.5 was used. The minimal isoelectric point is 6.0 The concentrate is diluted to a solution with 3 wt. % protein in a volume of 1600 ml. The pH was adjusted to the values giving in Table 1. The process flow diagram from the three processing routes is given in FIG. 1.

Route A is a heat treatment at 65-90° C. for 30 minutes at a pH of 3.0-4.5 and in the presence of more than 60 mM NaCl. This treatment leads to a gel formation.

In Route B at an ionic strength of below 60 mM, a heat treatment of 30 minutes in a waterbath of 90° C. does not lead to gel formation. The trypsin protease inhibitor activity is however reduced down to <10% of the original activity. The liquid is cooled down to room temperature. Gel formation is induced in Route B by increasing the ionic strength above 60 mM after the heat treatment.

Part of the heat treated protease inhibitor solution of Route B (970 ml) is separated and freeze dried (Route C). This yields a dried heat inactivated protease inhibitor isolate. After dissolving the powder a clear solution is obtained that can form a gel at room temperature after setting the ionic strength above 60 mM by addition of NaCl. In these experiments the ionic strength was increased to 200 mM. Gelling occurs at room temperature or at elevated temperature.

TABLE 1

Recipe for the three gel formation routes

|  | Cold salt induced gel formation | | | Heated salt induced gel formation | |
|---|---|---|---|---|---|
|  | Freeze dried | | Concentrate Sample | Freeze dried | |
|  | 1 | 2 | 3 | 4 | 5 | 6 |
| Route in Scheme | C | C | B | B | C | C |
| Protease inhibitor isolate (wt. %) | 4 | 8 | 4 | 8 | 4 | 8 |
| NaCl (wt. %) | 0.6 | 0.6 | 0.6 | 0.6 | 0.6 | 0.6 |
| Water (wt. %) | 95.4 | 91.4 | 95.4 | 91.4 | 95.4 | 91.4 |
| pH | 3.5 | 3.0 | 3.5 | 3.0 | 3.5 | 3.0 |
| Gel strength load (g)* | 40 | 26 | 220 | 220 | 205 | 235 |

*The gel strength was measured using a Stevens-lifra texture analyser, Conditions: distance 40 mm, speed 2.0 mm/s.

The time of gel formation and gel strength depends on the concentration of protein, salt concentration and pH. High protein and salt concentration increase the speed of gel formation. Sample 1 and 2 were measured after 17 hours. A relatively weak gel was formed under those conditions. However, heating up to 30-80° C. increases the gel formation and the strength after addition of salt up to gel strengths obtained via Route C.

The time to obtain a salt induced gel at room temperature can be controlled from some minutes to several hours.

This example shows that a protease inhibitor isolate can be heat inactivated to form a pre-activated gelling powder. Gelling can be induced by salt at room temperature and elevated temperatures.

Example 1 also shows that a stable pre-activated protease inhibitor solution can be obtained that forms gels after addition of salt. Alternatively the pre-activated protease inhibitor solution can be added to a food blend or other salt rich mixture. The processing conditions can be optimised to obtain a desired gel strength or viscosity in time.

Example 2

Fortification and Structuring of a Sports Drink

A sports drink with a pH of 3.5 brand was mixed with the heat inactivated protease inhibitor powder obtained after freeze drying in Route C of Example 1. In total 4 wt. % of protein was added to the drink. The viscosity of the liquid was increased, but no solid gel was formed. The drink was a clear solution with no bitter taste by the protein added. This drink is very suitable as a high protein drink with a balanced amino acid profile.

Example 3

Instant Gel Formation with Potassium, Sodium and Calcium Ions

Gels were made using procedure A, B and C according to FIG. 1. Next to sodium, potassium ions and calcium ions were used to form gels and salt induced gels. The effective levels of calcium ions were found to be much lower. At high calcium levels a milky coagulum is formed. The results are shown in Table 2.

TABLE 2

Properties of protein solutions after a heat treatment at 90° C. for 30 minutes at pH 3.5 at 4 wt. % protein dosing.

|  | Concentration (mM) | Appearance | Gel strength load (g)* |
|---|---|---|---|
| NaCl | 50 | viscous liquid | 93 |
|  | 100 | strong opaque gel | 276 |
|  | 150 | milky viscous paste | 39 |
| KCl | 50 | clear gel | 141 |
|  | 100 | opaque strong gel | 180 |
|  | 150 | viscous milky paste | 43 |
| CaCl$_2$ | 50 | clear gel | 369 |
|  | 100 | viscous milky paste | 50 |
|  | 150 | milk | 32 |

*The gel strength was measured using a Stevens-lifra texture analyser, Conditions: distance 40 mm, speed 2.0 mm/s.

Example 4

Appearance of Heat Treated Protease Inhibitor Isolate Gels

Native potato protease inhibitor isolate solution is heated at 90° C. for 30 minutes while the pH is adjusted with NaOH or HCl. The appearance of the gel is classified in 6 classes using the codes described in the legend.

Table 3 shows the various conditions that can be employed to obtain a desired gel and viscosity property. Even at low protein concentrations conditions can be set to obtain a clear gel.

TABLE 3

| | 1% protein | | | | | 2% protein NaCl mM | | | | | 3% protein | | | | |
|---|---|---|---|---|---|---|---|---|---|---|---|---|---|---|---|
| pH | 20 | 60 | 100 | 200 | 400 | 20 | 60 | 100 | 200 | 400 | 20 | 60 | 100 | 200 | 400 |
| 2.6 | 1 | 1 | 1 | 1 | 6 | 1 | 1 | 1 | 3 | 6 | 1 | 1 | 1 | 1 | 6 |
| 2.7 | 1 | 1 | 1 | 1 | 6 | 1 | 1 | 1 | 3 | 6 | 1 | 1 | 1 | 1 | 6 |
| 2.8 | 1 | 1 | 1 | 1 | 6 | 1 | 1 | 1 | 3 | 6 | 1 | 1 | 1 | 1 | 6 |
| 2.9 | 1 | 1 | 1 | 1 | 6 | 1 | 1 | 1 | 3 | 6 | 1 | 1 | 1 | 1 | 6 |
| 3.0 | 1 | 1 | 1 | 3 | 6 | 1 | 1 | 1 | 3 | 6 | 1 | 1 | 1 | 3 | 6 |
| 3.1 | 1 | 1 | 1 | 3 | 6 | 1 | 1 | 1 | 3 | 6 | 1 | 1 | 1 | 3 | 6 |
| 3.2 | 1 | 1 | 1 | 3 | 6 | 1 | 1 | 1 | 3 | 6 | 1 | 1 | 1 | 3 | 6 |
| 3.3 | 1 | 1 | 1 | 3 | 6 | 1 | 1 | 1 | 3 | 6 | 1 | 1 | 1 | 3 | 6 |
| 3.4 | 1 | 1 | 1 | 4 | 6 | 1 | 1 | 2 | 4 | 6 | 1 | 1 | 1 | 4 | 6 |
| 3.5 | 1 | 1 | 3 | 4 | 6 | 1 | 1 | 3 | 4 | 6 | 1 | 1 | 3 | 4 | 6 |
| 3.6 | 1 | 1 | 3 | 6 | 6 | 1 | 2 | 3 | 4 | 6 | 1 | 1 | 3 | 6 | 6 |
| 3.7 | 1 | 1 | 3 | 6 | 6 | 1 | 3 | 3 | 4 | 6 | 1 | 1 | 3 | 6 | 6 |
| 3.8 | 1 | 3 | 3 | 6 | 6 | 1 | 3 | 3 | 6 | 6 | 1 | 3 | 3 | 6 | 6 |
| 3.9 | 1 | 3 | 4 | 6 | 6 | 1 | 3 | 3 | 6 | 6 | 1 | 3 | 4 | 6 | 6 |
| 4.0 | 1 | 3 | 4 | 6 | 6 | 1 | 4 | 4 | 6 | 6 | 1 | 3 | 4 | 6 | 6 |

TABLE 3-continued

| pH | 4% protein | | | | | 8% protein NaCl mM | | | | | 12% protein | | | | |
| --- | --- | --- | --- | --- | --- | --- | --- | --- | --- | --- | --- | --- | --- | --- | --- |
| | 20 | 60 | 100 | 200 | 400 | 20 | 60 | 100 | 200 | 400 | 20 | 60 | 100 | 200 | 400 |
| 4.1 | 1 | 4 | 6 | 6 | 6 | 1 | 4 | 4 | 6 | 6 | 1 | 4 | 6 | 6 | 6 |
| 4.2 | 1 | 4 | 6 | 6 | 6 | 1 | 4 | 4 | 6 | 6 | 1 | 4 | 6 | 6 | 6 |
| 4.3 | 1 | 6 | 6 | 6 | 6 | 1 | 4 | 4 | 6 | 6 | 1 | 6 | 6 | 6 | 6 |
| 4.4 | 1 | 6 | 6 | 6 | 6 | 1 | 6 | 6 | 6 | 6 | 1 | 6 | 6 | 6 | 6 |
| 4.5 | 1 | 6 | 6 | 6 | 6 | 1 | 6 | 6 | 6 | 6 | 1 | 6 | 6 | 6 | 6 |
| 4.6 | 1 | 6 | 6 | 6 | 6 | 1 | 6 | 6 | 6 | 6 | 1 | 6 | 6 | 6 | 6 |
| 4.7 | 1 | 6 | 6 | 6 | 6 | 1 | 6 | 6 | 6 | 6 | 1 | 6 | 6 | 6 | 6 |
| 4.8 | 1 | 6 | 6 | 6 | 6 | 1 | 6 | 6 | 6 | 6 | 1 | 6 | 6 | 6 | 6 |
| 4.9 | 1 | 6 | 6 | 6 | 6 | 1 | 6 | 6 | 6 | 6 | 1 | 6 | 6 | 6 | 6 |
| 5.0 | 1 | 6 | 6 | 6 | 6 | 5 | 6 | 6 | 6 | 6 | 1 | 6 | 6 | 6 | 6 |
| 5.1 | 1 | 6 | 6 | 6 | 6 | 5 | 6 | 6 | 6 | 6 | 1 | 6 | 6 | 6 | 6 |
| 5.2 | 6 | 6 | 6 | 6 | 6 | 5 | 5 | 5 | 6 | 6 | 6 | 6 | 6 | 6 | 6 |
| 5.3 | 6 | 6 | 6 | 6 | 6 | 5 | 5 | 5 | 6 | 6 | 6 | 6 | 6 | 6 | 6 |
| 5.4 | 6 | 6 | 6 | 6 | 6 | 5 | 5 | 5 | 6 | 6 | 6 | 6 | 6 | 6 | 6 |
| 2.6 | 1 | 1 | 1 | 3 | 6 | 1 | 1 | 3 | 3 | 5 | 0 | 3 | 3 | 4 | 4 |
| 2.7 | 1 | 1 | 1 | 3 | 6 | 1 | 1 | 3 | 4 | 5 | 0 | 3 | 3 | 4 | 4 |
| 2.8 | 1 | 1 | 1 | 3 | 6 | 1 | 1 | 3 | 4 | 5 | 0 | 3 | 3 | 4 | 4 |
| 2.9 | 1 | 1 | 1 | 3 | 6 | 1 | 1 | 3 | 5 | 5 | 1 | 3 | 3 | 4 | 4 |
| 3.0 | 1 | 1 | 1 | 4 | 6 | 1 | 2 | 3 | 5 | 5 | 1 | 3 | 3 | 4 | 4 |
| 3.1 | 1 | 1 | 1 | 4 | 6 | 1 | 2 | 3 | 5 | 5 | 1 | 3 | 3 | 4 | 4 |
| 3.2 | 1 | 1 | 1 | 4 | 6 | 2 | 3 | 3 | 5 | 5 | 3 | 3 | 3 | 4 | 4 |
| 3.3 | 1 | 1 | 1 | 4 | 6 | 2 | 3 | 3 | 5 | 5 | 3 | 3 | 3 | 4 | 4 |
| 3.4 | 1 | 1 | 3 | 6 | 6 | 3 | 3 | 3 | 5 | 5 | 3 | 3 | 3 | 4 | 4 |
| 3.5 | 1 | 3 | 3 | 6 | 6 | 3 | 3 | 4 | 5 | 5 | 3 | 3 | 4 | 4 | 4 |
| 3.6 | 1 | 3 | 3 | 6 | 6 | 3 | 3 | 4 | 5 | 5 | 3 | 3 | 4 | 4 | 4 |
| 3.7 | 1 | 3 | 3 | 6 | 6 | 3 | 4 | 4 | 5 | 5 | 3 | 4 | 4 | 4 | 4 |
| 3.8 | 1 | 3 | 3 | 6 | 6 | 3 | 4 | 5 | 5 | 5 | 3 | 4 | 4 | 4 | 4 |
| 3.9 | 1 | 3 | 3 | 6 | 6 | 3 | 5 | 5 | 5 | 5 | 3 | 4 | 4 | 4 | 4 |
| 4.0 | 1 | 4 | 4 | 6 | 6 | 3 | 5 | 5 | 5 | 5 | 4 | 4 | 4 | 4 | 4 |
| 4.1 | 1 | 4 | 4 | 6 | 6 | 3 | 5 | 5 | 5 | 5 | 4 | 4 | 4 | 4 | 4 |
| 4.2 | 3 | 4 | 4 | 6 | 6 | 3 | 5 | 5 | 5 | 5 | 4 | 4 | 4 | 4 | 4 |
| 4.3 | 3 | 4 | 4 | 6 | 6 | 3 | 5 | 5 | 5 | 5 | 4 | 4 | 4 | 4 | 4 |
| 4.4 | 4 | 4 | 4 | 6 | 6 | 5 | 5 | 5 | 5 | 5 | 4 | 4 | 4 | 4 | 4 |
| 4.5 | 4 | 6 | 4 | 6 | 6 | 5 | 5 | 5 | 5 | 5 | 4 | 4 | 4 | 4 | 4 |
| 4.6 | 4 | 6 | 4 | 6 | 6 | 5 | 5 | 5 | 5 | 5 | 4 | 4 | 4 | 4 | 4 |
| 4.7 | 4 | 6 | 4 | 6 | 6 | 5 | 5 | 5 | 5 | 5 | 4 | 4 | 4 | 4 | 4 |
| 4.8 | 4 | 6 | 6 | 6 | 6 | 5 | 5 | 5 | 5 | 5 | 4 | 4 | 4 | 4 | 4 |
| 4.9 | 4 | 6 | 6 | 6 | 6 | 5 | 5 | 5 | 5 | 5 | 4 | 4 | 4 | 4 | 4 |
| 5.0 | 4 | 6 | 6 | 6 | 6 | 5 | 5 | 5 | 5 | 5 | 4 | 4 | 4 | 4 | 4 |
| 5.1 | 4 | 6 | 6 | 6 | 6 | 5 | 5 | 5 | 5 | 5 | 4 | 4 | 4 | 4 | 4 |
| 5.2 | 6 | 6 | 6 | 6 | 6 | 5 | 5 | 5 | 5 | 5 | 4 | 4 | 4 | 4 | 4 |
| 5.3 | 6 | 6 | 6 | 6 | 6 | 5 | 5 | 5 | 5 | 5 | 4 | 4 | 4 | 4 | 4 |
| 5.4 | 6 | 6 | 6 | 6 | 6 | 5 | 5 | 5 | 5 | 5 | 4 | 4 | 4 | 4 | 4 |

Legend to Table 3
Gel appearance
1 = Liquid clear
2 = Liquid viscous clear
3 = Gel clear
4 = Gel opaque
5 = Paste milky
6 = Liquid milky

The invention claimed is:

1. A method of forming a gel, comprising the steps of
providing an aqueous solution of native potato protease inhibitor isolate having an isoelectric point of at least 6.0, and a molecular weight of less than 35 kDa;
wherein the concentration of native potato protease inhibitor in the solution is at least 3 wt. %, based on the total weight of the solution;
subjecting the native potato protease inhibitor solution to a heat treatment to a temperature of 65-121° C. for 10-60 minutes, or an UHT treatment at temperatures above 121° C., at an ionic strength of less than 60 mM and a pH of 3.0-4.5 yielding a heat treated native potato protease inhibitor solution; and
setting the ionic strength of the native potato protease inhibitor solution to at least 60 mM.

2. A method according to claim 1, wherein the ionic strength of the heat treated native potato protease inhibitor solution is set to more than 60 mM by the addition of at least one salt.

3. A method according to claim 1, wherein the ionic strength of the native potato protease inhibitor solution is set to more than 60 mM by adding the heat treated native potato protease inhibitor solution to a composition comprising at least one salt.

4. A method according to claim 1, wherein the native potato protease inhibitor isolate has a glycoalkaloid concentration of less than 150 ppm.

5. A method according to claim 1, wherein the native potato protease inhibitor is isolated from *Solanum tuberosum*.

6. A method according to claim 1, wherein the native potato protease inhibitor isolate has an isoelectric point of 6.0-9.0.

7. A method according to claim 1, wherein the heat treatment comprises heating to a temperature of 85-100° C. for at least 10 minutes, or an UHT treatment at temperatures above 121° C.

8. A method according to claim 1, wherein the ionic strength of the native potato protease inhibitor solution is set to 60-4000 mM.

9. A method according to claim 2, wherein the at least one salt comprises a cation selected from the group consisting of sodium, potassium and calcium ions.

10. A method according to claim 1, wherein the transparency and/or the viscosity of the gel is controlled by the ionic strength set.

11. A method according to claim 1, wherein the heat treated native potato protease inhibitor solution is freeze dried, flash dried or spray dried and subsequently dissolved in water prior to setting the ionic strength to more than 60 mM.

12. A method according to claim 11, comprising the additional step of heating the native potato protease inhibitor solution with an ionic strength of more than 60 mM to a temperature of 65-121° C.

13. A method according to claim 1 wherein the isoelectric point of the aqueous solution of native potato protease inhibitor isolate is more than 7.0.

14. A method according to claim 1 wherein the molecular weight of the aqueous solution of native potato protease inhibitor isolate is less than 23 kDa.

15. A method according to claim 1, wherein the concentration of native potato protease inhibitor in the solution is at least 4 wt. % based on the total weight of the solution.

16. A method according to claim 8 wherein the ionic strength of the native potato protease inhibitor solution is set to 60-400 mM.

17. A method according to claim 12, wherein the temperature of the native potato protease inhibitor solution is set to a temperature of 85-100° C.

* * * * *